United States Patent [19]
Cooper et al.

[11] Patent Number: 4,465,864
[45] Date of Patent: Aug. 14, 1984

[54] PROCESS OF HYDROXYLATION OF AN AROMATIC CARBONYL COMPOUND

[75] Inventors: Geoffrey K. Cooper, Shelton; Lewis G. Harruff, Grapeview, both of Wash.

[73] Assignee: International Telephone and Telegraph Corporation, New York, N.Y.

[21] Appl. No.: 404,543

[22] Filed: Aug. 2, 1982

[51] Int. Cl.³ .................. C07C 45/61; C07C 37/00
[52] U.S. Cl. .................................. 568/433; 568/763; 562/475; 562/476
[58] Field of Search ............... 568/629, 433; 570/206; 562/475

[56] References Cited

U.S. PATENT DOCUMENTS 3,160,653 12/1964 Benning et al. ............... 568/433 X
3,413,341 11/1968 Bursack et al. ............... 568/629 X
4,240,987 12/1980 Martin et al. ..................... 570/206

Primary Examiner—Bernard Helfin
Attorney, Agent, or Firm—James B. Raden; Harold J. Holt

[57] ABSTRACT

An aromatic compound is hydroxylated by reacting the aromatic compound in an aqueous solvent with a triiodide salt to form a reaction mixture containing the corresponding iodoaromatic compound. The mixture is reacted, without separating the iodoaromatic compound, with a hydroxylating agent to form the corresponding hydroxy aromatic compound. The iodide salt, formed as a by-product of the reaction, is then separated for reuse in the process.

11 Claims, No Drawings

PROCESS OF HYDROXYLATION OF AN AROMATIC CARBONYL COMPOUND

This invention relates to a process for the hydroxylation of an aromatic compound.

Lignin derived aromatic compounds are frequently inexpensive precursors of a number of valuable organic substances. For example, vanillin is an important precursor chemical of 3,4,5-trimethoxybenzaldehyde, a chemical of well known importance to the pharmaceutical industry. However, known processes for the conversion of vanillin to trimethoxybenzaldehyde have certain drawbacks. U.S. Pat. No. 3,855,306 describes one such process in which vanillin is brominated to produce 5-bromovanillin using bromine and a concentrated hydrobromic acid solvent. The resulting 5-bromovanillin is then isolated from the reaction mixture and hydrolyzed to the corresponding hydroxyvanillin with sodium hydroxide and a copper catalyst. The resulting reaction mixture includes sodium bromide which is normally not recycled but rather is discarded or used elsewhere. Moreover, bromine and hydrobromic acid are both highly corrosive and hazardous to handle.

Other halogenated vanillin derivatives include 5-chlorovanillin and 5-iodovanillin. It is known however that chlorovanillin is unreactive toward hydroxide ion/copper and yields no hydroxyvanillin using conditions even more drastic than those effective for converting 5-bromovanillin to 5-hydroxyvanillin. Aryl iodides, on the other hand, are known to be more reactive than the corresponding bromocompounds in this kind of reaction. Iodine, however, would be prohibitively expensive if discarded as the bromine is in the above described bromination reaction. Reference to the iodination of vanillin to 5-iodovanillin may be found in H. Erdman, Svensk. Kem. Tids., 47, 223 (1935) Chem. Abstr. 30:449. Conversion of 5-iodovanillin to 5-hydroxyvanillin is disclosed in S. Banerjee, M. Manolopoulo and J. M. Pepper, Canadian Journal of Chemistry, 40, 2175 (1962). However, the processes there disclosed isolate the intermediate iodovanillin before hydrolysis and do not recover the by-product iodide ion from the various reactions.

A process has now been discovered from the conversion of armoatic compounds to hydroxy aromatic compounds which does not isolate an intermediate haloaromatic compound and which permits economical recovery and reuse of halide by-products produced during the reaction. The process involves the hydroxylation of an aromatic compound by reacting the aromatic compound in the presence of an aqueous solvent with a triiodide salt to form a reaction mixture containing the corresponding iodoaromatic compound, reacting the mixture, without separation of the iodoaromatic compound with a hydroxylating agent to form the corresponding hydroxy aromatic compound and additional iodide salt, separating the hydroxy aromatic compound from the iodide salt and recapturing the iodide salt. The corresponding alkoxy aromatic compound may be produced by alkylation of the hydroxy aromatic compound by known alkylation procedures.

The process of the invention renders cost-effective an otherwise cost-ineffective process using the iodination route. In the case of such processes as the conversion of vanillin to trimethoxybenzaldehyde, the process becomes basically a one-step or "one-pot" process by eliminating the purification of the intermediate 5-iodovanillin. Iodination of vanillin and conversion of the resulting iodovanillin to hydroxyvanillin may be carried out in the same reaction vessel. Moreover, efficient recycle of the by-product iodide salt to the triiodide reagent used in the reaction obviates the need to dispose of the valuable iodine/iodide material. Prior art processes necessarily separated and recovered the bromide or iodide by-product from the halogenation reaction and again from the hydroxylation reaction. In the present process, the iodide salt is recovered only after hydroxylation, at which time it may be oxidized to iodine and the iodine partially reduced to form the starting triiodide reactant. (The triiodide reagent is a solution of iodine in an excess of the iodide salt, e.g., $NaI + I_2$ or $NaI_3$). If chlorine is used as the oxidizing agent, the only net by-product of the reaction is sodium chloride, an obviously inexpensive waste by-product.

The starting materials useful in the practice of the invention are aromatic compounds subject to electrophilic substitution reactions. Such compounds may include benzene but the process is particularly suitable for aromatic compounds containing electron donating nuclear substituents, i.e. mono- or polycyclic aromatic compounds containing one or more hydrocarbon substituents such as an alkyl, cycloalkyl, aryl or aralkyl group and/or one or more hydroxy groups or aldehyde, acid, ester or ether radicals, i.e., alkoxy, carboxy, carboxyl or aldehyde carbonyl groups. The process is not useful with substituents such as poly-nitro, or ketone groups with an alpha hydrogen, which either react with the reagent or strongly de-activate the ring. Ketone groups are deactivating, as are aldehyde groups, but ketones containing an alpha hydrogen would react with the iodinating agent whereas the aldehydes would not. For example, diaryl ketones would not interfere. Only in the case of severely de-activating groups, such as poly-nitro groups, is the de-activation a problem in carrying out the iodination. Weakly de-activating groups such as aldehyde groups do not interfere with iodination. Useful aromatic compounds are simple monohydric phenols such as phenol, o-, m- and p-cresol and guaiacol; polyhydric phenols such as catechol and resorcinol; phenolic aldehydes such as protocatechualdehyde, vanillin, syringaldehyde, p-hydroxybenzaldehyde and 5-formylvanillin; phenolic acids such as vanillic acid, syringic acid, protocatechuic acid and p-hydroxybenzoic acid. The preferred aromatic reactants are those having at least one phenolic hydroxyl functionality.

The first step of the reaction involves iodination of the aromatic compound with the triiodide salt in the presence of water as a solvent. The water should contain from 0.7 to 1.25 molar equivalents of a hydroxide, preferably an alkali metal hydroxide, and from 1–2 molar equivalents of an alkali metal triiodide (e.g. iodine plus sodium iodide). The aqueous solvent should also contain from 0.1 to 20 mole % of an acid catalyst, which may be a mineral acid such as sulfuric, hydrochloric or phosphoric acid. Reaction is carried out at temperatures ranging from 20°–120° C. If the starting compound contains a nuclear substituent, iodination will occur in the ortho or para position on the nuclear ring.

The subsequent step of the reaction, hydroxylation, is carried out directly with the reaction mixture from iodination without any intermediate isolation or other processing of the reactants or by-products. A base, such as an alkali metal hydroxide or a quaternary amine such as tetraalkylammonium hydroxide, is added directly to the reaction mixture to make a final concentration of 0.5 to 6 molar, with 0.1 to 20 mole % copper metal, or cuprous salts such as oxide, chloride or iodide, at temperatures of from 50°–120° C. The preferred conditions are addition of sodium hydroxide to the iodination reaction mixture to give a concentration of 2–5 molar, then addition of 1–5 mole % copper dust, cuprous oxide or cuprous chloride, then allowing reaction at reflux (100°–120° C.) for about 18 hours.

The sodium or other iodide ion by-product may be recovered by neutralizing the caustic in the reaction mixture with an acid such as sulfuric or hydrochloric, extracting the organic product from the water solvent and then treating the water solution with an oxidizing agent. The oxidizing agent may be chlorine, sodium hypochlorite, hydrogen peroxide, persulfate, perborate or electrochemical oxidation may be used. The iodine which precipitates is then recovered from the water solvent by filtration, solvent extraction or distillation/sublimation. The temperature of the water phase may be from 0° to 100° C. The preferred method for iodine recovery is treatment of the water solution with sulfuric acid to neutralize the base, extraction of the hydroxy aromatic compound with organic solvents such as methylene chloride or toluene, oxidation with chlorine or electrochemically and filtration or solvent extraction to recover the iodine. The crude hydroxy aromatic compound may then be used directly in any subsequent alkylation procedure.

A specific description of a preferred practice of the invention with vanillin as the aromatic compound is as follows. Vanillin is dissolved in water with one molar equivalent of sodium hydroxide while the solution is warmed to 50°–100° C. One molar equivalent of iodine and two molar equivalents of sodium iodide are added to water to prepare one molar equivalent of $NaI_3 \cdot NaI$. This sodium triiodide solution is added to the sodium vanillate solution along with a catalytic amount of sulfuric acid—preferably from 5 to 10 mole %. The mixture is stirred about one hour at a temperature of 50°–100° C., then sodium hydroxide is added to make the solution alkaline (from 1 to 5N). The copper catalyst is then added and the mixture heated at reflux until the iodovanillin is consumed, about 12 hours. The excess hydroxide is then neutralized and the 5-hydroxyvanillin extracted with a water-immiscible organic solvent. The aqueous phase bearing the sodium iodide is then subjected to oxidizing conditions and the resultant iodine precipitates from solution. The solid element is filtered out, and a sodium triiodide solution prepared by reducing a portion of the iodine to sodium iodide and dissolving the iodine in the iodide to make the sodium triiodide solution.

Alkylation of the hydroxy aromatic compound to the corresponding alkoxy aromatic compound may be performed in accordance with known alkylation procedures in which the hydroxy aromatic compound is reacted with an alkyl sulfate, alkyl halide or alkyl sulfonate in a suitable solvent, usually water, containing a base such as sodium hydroxide. Such reactions are shown at various places in the literature, as for ex. in Organic Synthesis, Col. Vol. II, page 619, 1943, in which veratraldehyde is prepared from vanillin. The iodide salt may, if desired, be recaptured subsequent to the alkylation reaction.

The following examples illustrate the practice of the invention. Unless otherwise indicated, all parts and percentages are by weight.

EXAMPLE 1

Vanillin (28.4 g, 200 mmole (millimole)) was dissolved in 1N NaOH (200 ml) and warmed to 90° C. to avoid precipitation of sodium vanillate. A 2 molar aqueous solution of $NaI_3 \cdot NaI$ (105 ml, 210 mmole $I_2$) plus 3.55 molar aqueous $H_2SO_4$ (5 ml) was added over 3 hours with stirring. The iodine color was discharged, and a pale tan stirrable precipitate formed. The solution was then cooled to room temperature, acidified to pH 2–3 with 20% aqueous $H_2SO_4$, and extracted with 10% methanol/90% chloroform. The organic phase was dried ($MgSO_4$) and the solvent stripped to yield 53 g (99%) of 5-iodovanillin, more than 95% pure as analyzed by nuclear magnetic resonance spectroscopy (NMR).

EXAMPLE 2

Vanillin (3.04 g., 20 mmole) was dissolved in 1N sodium hydroxide solution (20 ml), and warmed to 80° C. Then a solution of $NaI_3 \cdot NaI$ (2N) in water (10.1 ml) plus 20% aqueous $H_2SO_4$ (0.5 ml) was added dropwise over 30 minutes, and the mixture stirred an additional 30 minutes. Sodium hydroxide (7.6 ml of 50% solution), and copper dust (128 mg = 10 mole %) were then added and the mixture heated at reflux overnight. The solution was cooled, filtered to recover catalyst, neutralized with 20% aqueous $H_2SO_4$, and extracted thoroughly with chloroform. The organic base was dried ($Na_2SO_4$) and stripped to yield 3.1 g (99%) of organic material consisting of 75% 5-hydroxyvanillin and 25% vanillin.

The aqueous phase was concentrated under vacuum, and treated with the theoretical quantity of chlorine as a water solution. The purple iodine crystals were removed by filtration. As 87% recover of iodine was achieved.

EXAMPLE 3

Vanillin (2.84 g, 20 mmole) was dissolved in 1N NaOH (20 ml) at 80° C., then a mixture of 2N ($NaI_3 \cdot NaI$)/$H_2O$ (10.1 ml = 20.2 mmole $I_2$) plus 20% aqueous $H_2SO_4$ (0.5 ml = 8 mole %) was added dropwise over 30 minutes. A tan precipitate formed. The reaction mixture was stirred an additional 3.5 hours. A 10% solution of $Na_2S_2O_3$ (1.5 ml) was added to reduce excess iodine, then 50% aqueous NaOH (7.6 ml) was added (to make 4N in NaOH), plus copper dust (128 mg, 2 mmole, 10 mole %) added. The mixture was refluxed overnight, cooled to room temperature, filtered to remove catalyst, the pH was adjusted to 2 with 20% aqueous $H_2SO_4$, and the solution extracted 5X with 20% methanol/80% chloroform. A yield of 3.1 g (99%) of product was obtained, which NMR showed to consist of about 75% 5-hydroxyvanillin and 25% vanillin.

Example 3 was repeated using concentrations of NaOH base ranging from 1N to 6N, using KOH and LiOH in place of NaOH as the base for the iodination procedure. All gave substantially equivalent results.

Example 3 was also repeated using from 5 to 10 mole % of cuprous oxide, cuprous chloride, cuprous iodide and copper dust, as the catalyst for conversion of the iodovanillin to hydroxyvanillin. Recovery of 5-hydroxyvanillin was 80–85% (remainder vanillin) with copper dust, from 70–80% with the copper oxide or salts.

EXAMPLE 4

Vanillin (20 mmole) was iodinated and converted to 5-hydroxyvanillin as set forth in Examples 1–3. The aqueous phase from the extraction of 5-hydroxyvanillin (theoretically containing 80.8 mmole NaI) was then concentrated in vacuum to remove dissolved volatile organics, then chlorine water [42 mmole $Cl_2 = 500$ ml of 0.086M (0.61%) chlorine water] was added slowly. The iodine precipitate was filtered off and washed with water. To determine the quantity recovered, the iodine was washed off the filter with 2N sodium iodide solution (300 ml), and then titrated (at pH 5) with 0.2N sodium thiosulfate solution until the iodine color disappeared. A quantity of 350 ml of the 0.2N thiosulfate was consumed showing that 70 mmole $I_2$ was recovered, an efficiency of 87%.

The process thus provides an essentially one-step process for the nearly quantitative conversion of aromatic compounds to hydroxy aromatic compounds and for the recovery and recycle of the reagent used for conversion.

We claim:

1. A process for the hydroxylation of a phenolic carbonyl compound to the corresponding hydroxylated phenolic carbonyl compound comprising the sequential steps of reacting the phenolic carbonyl compound in the presence of an aqueous solvent with at least one molar equivalent of an alkali metal triiodide salt, said aqueous solvent containing an alkali metal hydroxide and an acid catalyst, to form a reaction mixture containing the corresponding iodoaromatic compound and an iodide salt, reacting said mixture, without separation of the iodoaromatic compound, with a hydroxylating agent comprising a hydroxide and a copper catalyst to form the correspond hydroxylated phenolic carbonyl compound and additional iodine salt, separating said hydroxylated phenolic carbonyl compound from said iodide salt and recapturing said iodide salt for reuse in said process.

2. The process of claim 1 in which the aromatic compound is hydroxylated in the ortho or para position.

3. The process of claim 2 in which the aromatic compound contains both an aldehyde and a hydroxy or alkoxy nuclear substituent.

4. The process of claim 3 in which the aromatic compound is vanillin and the hydroxy aromatic compound is 5-hydroxyvanillin.

5. The process of claim 1 in which the aromatic compound is reacted with the triiodide salt in the presence of an aqueous solvent containing from 0.7 to 1.25 molar equivalents of an alkali metal hydroxide.

6. The process of claim 5 in which the aromatic compound is reacted with the triiodide salt in the presence of from 0.1 to 20 mole % of an acid catalyst.

7. The process of claim 1 in which the hydroxylating agent comprises from 0.5 to 6 molar of an hydroxide and from 0.1 to 20 mole % of a catalyst selected from the group consisting of copper metal, cuprous oxides and cuprous salts.

8. The process of claim 1 in which the iodide salt after recapture is oxidized to iodine for reuse in said process.

9. The process of claim 8 in which the iodide salt is oxidized with chlorine.

10. The process of claim 1 in which the hydroxy aromatic compound is separated from the iodide salt by neutralizing the reaction mixture and extracting the hydroxy aromatic compound with an organic solvent.

11. A process for the hydroxylation of vanillin to 5-hydroxyvanillin comprising the sequential steps of reacting vanillin in the presence of an aqueous solvent with at least one molar equivalent of an alkali metal triiodide salt, said aqueous solvent containing an alkali metal hydroxide and an acid catalyst, to form a reaction mixture containing 5-iodovanillin and an iodide salt, reacting said mixture, without separation of the 5-iodovanillin, with a hydroxylating agent comprising a hydroxide and a copper catalyst, to form 5-hydroxyvanillin, separating said 5-hydroxyvanillin from said iodide salt, recapturing said iodide salt and oxidizing said iodide to iodine for reuse in said process.

* * * * *